United States Patent [19]

Murakami et al.

[11] Patent Number: 5,017,798
[45] Date of Patent: May 21, 1991

[54] SURFACE EXAMINING APPARATUS FOR DETECTING THE PRESENCE OF FOREIGN PARTICLES ON TWO OR MORE SURFACES

[75] Inventors: Eiichi Murakami, Yokohama; Michio Kohno; Akiyoshi Suzuki, both of Tokyo, all of Japan

[73] Assignee: Canon Kabushiki Kaisha, Tokyo, Japan

[21] Appl. No.: 406,090

[22] Filed: Sep. 12, 1989

Related U.S. Application Data

[60] Division of Ser. No. 348,177, May 2, 1989, Pat. No. 4,886,975, which is a continuation of Ser. No. 14,034, Feb. 12, 1987, abandoned.

[30] Foreign Application Priority Data

| Feb. 14, 1986 | [JP] | Japan | 61-03062 |
| Mar. 20, 1986 | [JP] | Japan | 61-060871 |
| May 23, 1986 | [JP] | Japan | 61-118862 |
| May 23, 1986 | [JP] | Japan | 61-118863 |

[51] Int. Cl.$^5$ .................................. G01N 21/88
[52] U.S. Cl. ..................... 250/572; 356/431
[58] Field of Search ............ 250/572, 562, 563, 559, 250/571; 356/237, 239, 430, 431

[56] References Cited

U.S. PATENT DOCUMENTS

| 3,814,946 | 6/1974 | Takahashi et al. | 250/572 |
| 4,460,273 | 7/1984 | Koizumi et al. | 356/237 |
| 4,568,835 | 2/1986 | Imamura et al. | 250/572 |
| 4,610,541 | 9/1986 | Tanimoto et al. | 250/563 |

FOREIGN PATENT DOCUMENTS

129582 10/1977 Japan.

Primary Examiner—David C. Nelms
Attorney, Agent, or Firm—Fitzpatrick, Cella, Harper & Scinto

[57] ABSTRACT

An apparatus usable with an object having surfaces, for examining the states of the surfaces, includes on irradiating system for irradiating the surfaces of the object with a single light beam, and a plurality of light-receiving systems provided in association with the surfaces of the object, respectively, the plural light-receiving systems being arranged to receive light scatteringly reflected from the surfaces of the object, respectively, and to produce outputs corresponding to the states of the surfaces of the object, respectively.

12 Claims, 14 Drawing Sheets

SURFACE EXAMINING APPARATUS FOR DETECTING THE PRESENCE OF FOREIGN PARTICLES ON TWO OR MORE SURFACES

This application is a division of application Ser. No. 07/348,177 filed May 2, 1989, now U.S. Pat. No. 4,886,975, which application is a continuation of Ser. No. 07/014,034 filed Feb. 12, 1987, now abandoned.

FIELD OF THE INVENTION AND RELATED ART

This invention relates to a surface examining apparatus for detecting the state of a surface of an object and, more particularly, to a surface examining apparatus for detecting, with high-accuracy, the presence or absence of any dust or foreign particles adhered to a surface of an object. The examining apparatus of the present invention is particularly suitably usable in the field of manufacture of semiconductor devices such as integrated circuits, for detecting dust or foreign particles which are adhered to a plate-like member such as a reticle or photomask having a circuit pattern formed thereon, or which are adhered to a pellicle protecting film provided over the reticle or photomask.

The manufacture of semiconductor devices such as integrated circuits involves a photolithographic process wherein an exposure apparatus such as a stepper or a mask aligner is used to photolithographically transfer, onto a semiconductive or silicon wafer, a circuit pattern formed on a glass plate such as a reticle or photomask. If, in such photoprinting process, a photomask on which foreign particles are deposited is used, images of these foreign particles as well as an image of the circuit pattern of the photomask are photoprinted on the wafer, with the result that the yield of semiconductor devices is disadvantageously decreased. It is accordingly desired to examine the reticle or photomask, in the course of manufacture of semiconductor devices, so as to detect the presence or absence of any dust or foreign particles on such glass plate. There have been proposed various types of examining apparatuses and methods. Examples are disclosed in Japanese Laid-Open Patent Application, Laid-Open No. 162038/1981 filed by the assignee of the subject application, U.S. Pat. Nos. 4,468,120 and 4,541,475, Japanese Laid-Open Patent Applications, Laid-Open Nos. 12341/1984, 12342/1984 and 82727/1984.

FIG. 1 schematically shows a basic structure of a surface examining apparatus of the type such as disclosed in the aforementioned U.S. Pat. No. 4,468,120 and similar publications. In this type of examining apparatus, detection of a foreign particle is accomplished by utilizing the phenomenon that, when a light is incident on the foreign particle, it scatters the light, particularly isotropically or non-directionally.

In the structure illustrated in FIG. 1, a light beam from a laser 10 is directed by way of a scanning mirror 11 and a lens 12, along one of two alternating optical paths depicted by phantom lines in this Figure. The selection of these optical paths is made by moving a mirror 13 in opposite directions as denoted by a double-headed arrow. For the purpose of examination of an upper surface of a glass plate (reticle) 18, the mirror 13 is moved to the illustrated position so that the light beam from the lens 12 is reflected by the mirror 13 and by another mirror 14 toward the upper surface of the glass plate 18. For the purpose of examination of a lower surface of the glass plate 18, the mirror 13 is retracted so that the light beam from the lens 12 is reflected by a third mirror 15 toward the lower surface of the plate 18. In this manner, the light beam from the laser 10 is alternately incident on the upper and lower surfaces of the glass plate 18. By rotationally or vibrationally moving the scanning mirror 11, the upper or lower surface of the plate 18 is scanned along a line. Also, by moving the glass plate 18 in the direction of an arrow S1 or S2, the whole of the upper or lower surface of the plate 18 is scanned with the light beam from the scanning mirror 11. For the examination of the upper and lower surfaces of the glass plate 18, two sets of light-receiving units are provided at positions that are spaced from the path of a light directly reflected from the glass plate 18 and from the path of a light transmitted through the glass plate 18. In FIG. 1, light-receiving elements 16 and 17 are provided for the examination of the upper surface, are illustrated. On the basis of output signals from the light-receiving elements 16 and 17, the presence or absence of a foreign particle on the upper surface of the glass plate 18 is detected. More specifically, when the light beam from the laser 10 impinges on a foreign particle, it is scattered isotropically (non-directionally). Therefore, both the light-receiving elements 16 and 17 produce outputs of higher level. On the other hand, when the scanning light beam is incident on a circuit pattern formed on the glass plate 18, the light beam is diffractively reflected with specific direction, with the result that the photoreceptors 16 and 17 produce outputs of different signal levels. By comparing the outputs of the light-receiving elements 16 and 17, therefore, the existence of the foreign particle on the upper surface of the glass plate 18, in this case, is detected.

According to the FIG. 1 arrangement, however, the examination of the upper surface and the examination of the lower surface are executed alternately or sequentially with the introducing and retracting movement of the mirror 13. This requires longer time for the examination.

In an attempt to reduce the examination time, it may be possible to use a half mirror in place of the mirror 13 so as to execute the examination of the upper and lower surfaces of the glass plate 18 at the same time. In such a case, however, there is a high possibility that the light scattered by a particle on the lower surface of the glass plate enters into the light-receiving elements which are provided for the examination of the upper surface while, on the other hand, the light scattered by a particle on the upper surface of the glass plate enters into the light-receiving elements which are provided for the examination of the lower surface. Accordingly, it is difficult to accurately and discriminately examine the upper and lower surfaces of the glass plate.

In some cases, a reticle or photomask is protected by a pellicle protecting film such as illustrated at 31 in FIG. 2. When an examining and scanning light beam 30 impinges on a frame 32 of the pellicle protecting film 31, the material of the frame 32 reflects the light in scattered fashion, which disadvantageously causes degradation of the detecting accuracy for the dust or foreign particles.

SUMMARY OF THE INVENTION

It is accordingly a primary object of the present invention to provide a surface examining apparatus which assures examination of plural surfaces with high accuracy and at a higher speed.

It is another object of the present invention to provide a surface examining apparatus by which plural surfaces are examined discriminately without increasing the time for examination.

In accordance with one preferred form of the present invention, to achieve these objects, there is provided a surface examining apparatus for examining plural surfaces disposed in a "multilayer" fashion, wherein a single light beam is projected upon these surfaces to be examined. A plurality of discrete detecting means are provided in association with the plural surfaces, respectively, so as to detect light scattered by the plural respective surfaces, such that the states of the plural surfaces are examined independently of each other.

In accordance with another preferred form of the present invention, there is provided a surface examining apparatus for examining plural surfaces which are disposed in a "multilayer" fashion, wherein a light beam from a scanning optical system is divided into plural scanning beams which are projected, at one time, upon different positions on the plural surfaces so as to scan them simultaneously. A plurality of photodetecting means are provided so as to detect, independently or individually, light that is scattered by the plural respective surfaces in response to the irradiation of them with the scanning beams. In this manner, the states of the plural surfaces are detected independently of each other.

In accordance with a further preferred form of the present invention, there is provided a surface examining apparatus for examining plural surfaces which are disposed in a "multilayer" fashion, wherein provision is made to scan the plural surfaces with a plurality of light beams at one time. A plurality of detecting means are provided in association with the plural surfaces, respectively, so as to detect light caused by the scattering at the plural surfaces, respectively, thereby to examine the states of the plural surfaces independently of each other. The examining light beams are so projected that one or more lines of intersection, defined by intersecting planes that are determined by the scan of the examining light beams being projected upon the plural surfaces, do not intersect or lie on any one of the plural surfaces being examined.

In accordance with a still further preferred form of the present invention, there is provided a surface examining apparatus for examining plural surfaces which are disposed in a "multilayer" fashion, wherein a plurality of light beams are projected upon the plural surfaces, respectively, and a plurality of detecting means are provided in association with the plural surfaces, respectively, so as to detect light caused by the scattering at the plural surfaces, respectively, thereby to examine the states of the plural surfaces independently of each other. The examining light beams are so projected that a point of intersection, between (i) any one of the examining light beams impinging on a corresponding one of the plural surfaces and (ii) an axis (or its extension) of any one of the plural detecting means which is not associated with the aforementioned one surface, is located above or below all the plural surfaces.

These and other objects, features and advantages of the present invention will become more apparent upon a consideration of the following description of the preferred embodiments of the present invention taken in conjunction with the accompanying drawings.

DESCRIPTION OF THE PREFERRED EMBODIMENTS

Figure 1:
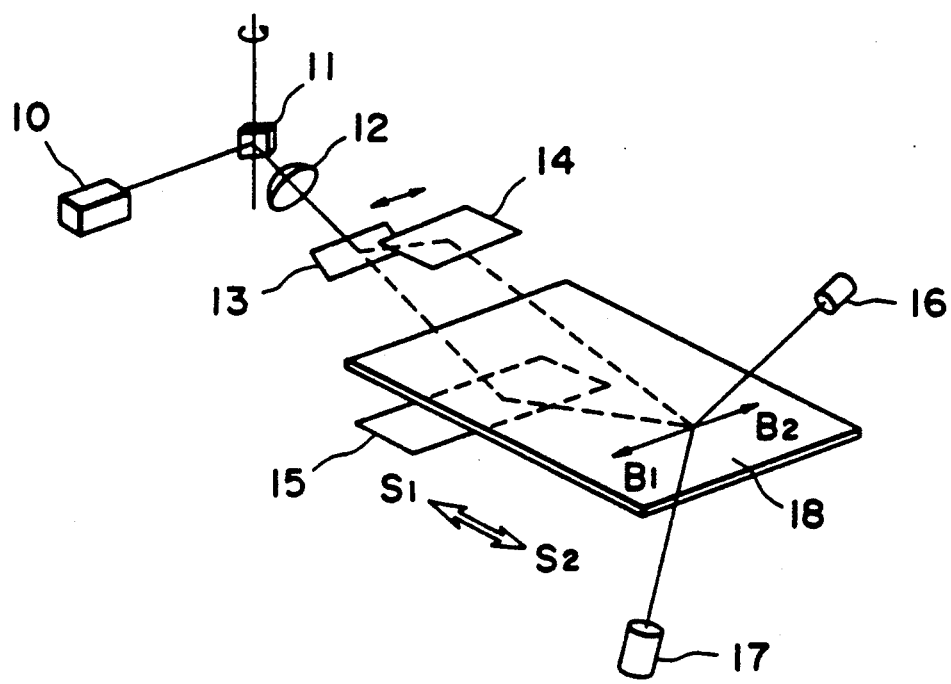
FIG. 1 is a schematic view showing the basic structure of a known type surface examining apparatus.
Figure 2:
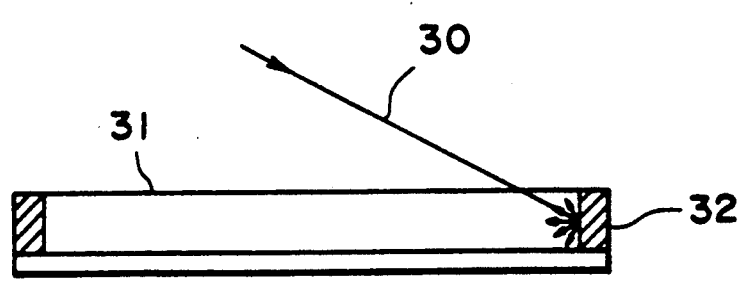
FIG. 2 is a schematic view illustrating a problem involved in the surface examination.
Figure 3:
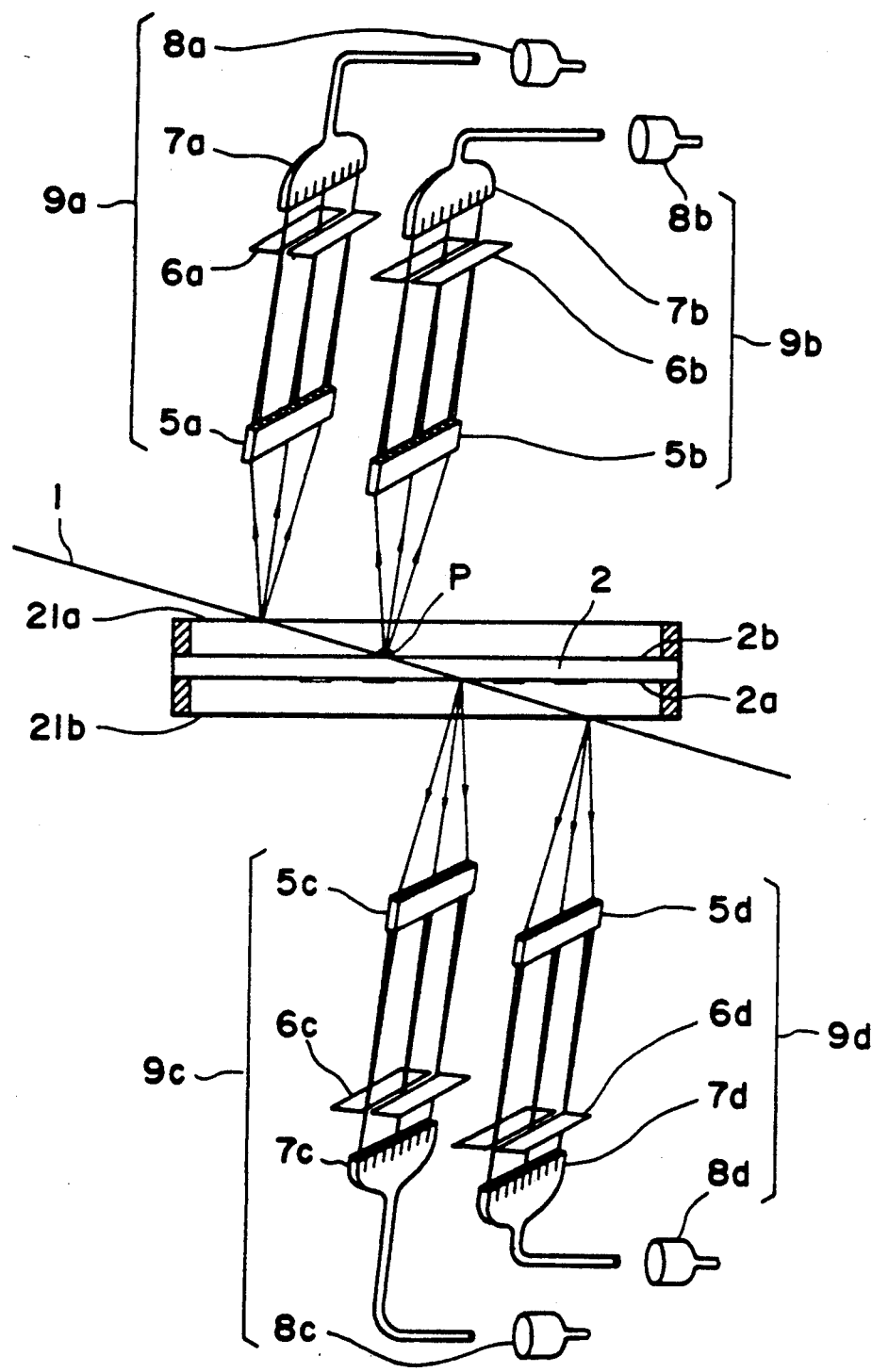
FIG. 3 is a schematic view showing an optical arrangement of a major portion of a surface examining apparatus according to an embodiment of the present invention.

Referring now to FIG. 3, there is shown an optical arrangement of a major portion of a surface examining apparatus according to an embodiment of the present invention.

The surface examining apparatus of the present embodiment includes a laser source, not shown, for producing a laser beam 1 which is scanningly deflected in a direction perpendicular to the sheet of the drawing by suitable scanning means such as a polygonal mirror, not shown. Denoted at reference numeral 2 is a reticle which is the subject of the examination. The reticle 2 comprises a glass plate having a light-transmissibility. The reticle 2 has surfaces 2a and 2b, on one (2a) of which a circuit pattern is formed. Pellicle protecting films 21a and 21b are provided so as to protect the upper and lower surfaces 2b and 2a of the reticle 2. Thus, in this embodiment, the upper surface of the upper pellicle protecting film 21a and the lower surface of pellicle protecting film 21b as well as the upper and lower surfaces 2b and 2a of the reticle 2, are the "surfaces" which are going to be examined. As shown in FIG. 3, the apparatus further includes four optical members 5a–5d each of which comprises a plurality of gradient-index type lens elements, such as Selfoc lenses (Trade Name), disposed in an array extending one-dimensionally. These optical members 5a–5d are positioned so that they are focused upon the surfaces 21a, 2b, 2a and 21b, respectively. The apparatus further includes field stops 6a–6d which are disposed in the vicinity of positions that are optically conjugate with the surfaces 21a, 2b, 2a and 21b, respectively. Also, the apparatus includes four light-guides 7a–7d for guidingly directing light beams, passed through the field stops 6a–6d, respectively, toward four photodetectors 8a–8d, respectively.

In the present embodiment, the optical member 5a, the field stop 6a, the light-guide 7a and the photodetector 8a are cooperative with each other to provide a first detecting means, denoted at 9a, which is associated with the examination of the surface 21a. Similarly, the optical members 5b–5d, the field stops 6b–6d, the light-guides 7b–7d and the photodetectors 8b–8d cooperate to provide second, third and fourth discrete detecting means, denoted at 9b, 9c and 9d, which are associated with the examination of the surfaces 2b, 2a and 21b, respectively.

In this embodiment, as shown in FIG. 3, the light beam 1 is projected upon the surfaces 21a, 2b, 2a and 21b from above at an incline. More specifically, the light beam 1 is so projected that it is incident on the surfaces 21a, 2b, 2a and 21b at different positions which are shifted from each other with respect to the horizontal direction as viewed in FIG. 3. Also, the light beam 1 is so projected that it passes through the four surfaces without impinging on frames of the pellicle protecting films.

If a particle P is adhered to the surface 2b, when the light beam 1 is incident on this particle P, the light beam 1 is scattered non-directionally. Since, in this case, the second detecting means 9b is focused upon the surface 2b, the optical member 5b of the second detecting means can collect the scattered light, (particularly, reflectively scattered light, in this embodiment) very efficiently. As a result, the photodetector 8b produces an output of increased level. On the other hand, the first, third and fourth detecting means 9a, 9c and 9d are defocused with respect to the surface 2b. Moreover, in the vicinity of the positions which are optically conjugate respectively with the surfaces 21a, 2a and 21b with respect to the optical members 5a, 5c and 5d of these detecting means, the field stops 6a, 6c and 6d are disposed, respectively, as described hereinbefore. Accordingly, the scattered light rays from the particle P on the surface 2b are sufficiently intercepted by means of the field stops 6a, 6c and 6d. As a result, the outputs of the photodetectors 8a, 8c and 8d are maintained substantially constant. Thus, by monitoring the output of the photodetector 8b, the particle P can be detected during the examination of the surface 2b.

In the present embodiment, as will be understood from the foregoing, the presence or absence of any foreign particles on the four surfaces is detected discriminately on the basis of the output signals from the four photodetectors 8a–8d. Also, for the whole-surface scan of the reticle 2 and the pellicle protecting films 21a and 21b, the reticle and the pellicle protecting films are moved as a unit relative to the scanning light beam 1 in the horizontal direction as viewed in FIG. 3. If, in such relative movement, the light beam 1 accidentally impinges on the pellicle film frame, the accuracy of surface examination in the apparatus of the present embodiment is not critically adversely affected thereby, since, the provision of the field stops 6a–6d effectively blocks reception of unwanted light from regions other than the specific points or areas which are to be examined. In other words, the photodetectors 8a–8d receive substantially only the scattered light rays from the surfaces 21a, 2b, 2a and 21b, respectively. The output signals from the photodetectors 8a–8d are transmitted to a signal processing unit, not shown, whereby the states of the surfaces 21a, 2b, 2a and 21b are finally determined or detected.

As described hereinbefore, each of the optical members 5a–5d of the present embodiment is provided by a combination of gradient-index type minute lens elements which are disposed in an array extending one-dimensionally. By this arrangement, the light-collecting portion of each detecting means can be made compact, while assuring high-efficiency collection of the scattered light rays from a foreign particle adhered to a surface being examined. It is to be noted that the combination of gradient-index type lens elements may be replaced by a cylindrical lens system or an array of bar lenses.

In the present embodiment, the scanning light beam 1 may be so projected that it is focused upon one of the four surfaces, e.g. the surface 2a of the reticle 2. In such a case, the light beam 1 in a strict sense is defocused with respect to the remaining surfaces to be examined. However, this is not inconvenient. Usually, such foreign particles on the pellicle surface or on the non-pattern bearing surface (2b) of the reticle 2, that must be considered in the photolithographic process, have a size or a particle diameter significantly larger than that of foreign particles on the pattern bearing surface (2a) of the reticle 2. Therefore, high detection accuracy is still attainable without the necessity of repeated examination with repeated irradiation of the light beam being sequentially focused upon the plural surfaces.

Figure 4:
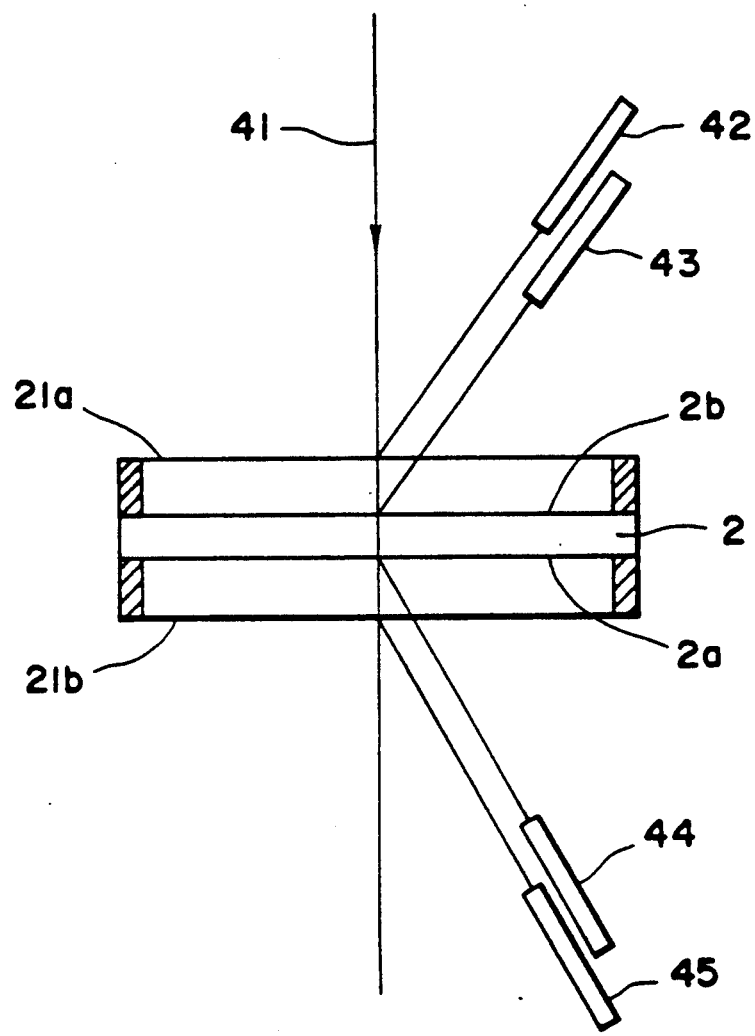
FIG. 4 is a schematic view showing a modified form of the surface examining apparatus shown in FIG. 3.

While, in the FIG. 3 embodiment, the light beam 1 is projected at an incline onto the surfaces from above, it may be perpendicularly incident on the surfaces to be examined. This arrangement is illustrated in FIG. 4. In this case, a light beam 41 is perpendicularly incident on the surfaces 21a, 2b, 2a and 21b while, on the other hand, first to fourth detecting means denoted by reference numerals 42–45 are disposed at an incline. Substantially the same advantageous effects are attainable with the illustrated arrangement.

In accordance with the embodiment described with reference to FIGS. 3 and 4, plural and discrete detecting means are provided and disposed in association with plural surfaces, being examined, as described hereinbefore. This assures that a single scanning operation with a single light beam is sufficient for detecting, easily, quickly and accurately, any foreign particle adhered to any one of the plural surfaces while discriminating such surface having the foreign particle. Therefore, a high-speed and high-accuracy surface examining apparatus is provided according to the present embodiment.

In the optical arrangement shown in FIG. 3, of the optical members 5a–5d is arranged so as to bring into an optically conjugate relation a corresponding one of the four surfaces and an entrance end (light-receiving surface) of a corresponding one of the light-guides 7a–7d. This forms a "finite imaging system". However, the optical members 5a–5d may be spaced from their respective surfaces to be examined by distances corresponding to their focal lengths, respectively, thus forming an "infinite imaging system".

The optically conjugate relation defined between each of the surfaces to be examined and a corresponding one of the light-guides 7a–7d and, thus, a corresponding one of the photodetectors 8a–8d, in this embodiment, is not essential. What is important is to arrange the apparatus so as to block entrance, into a particular detecting means, of unwanted light from surfaces other than a surface that is going to be examined by use of the particular detecting means.

Use of a single light beam for the examination purpose is not essential, and plural light beams may of course be used for the examination of plural surfaces, as will be described later with reference to several other preferred forms of the present invention. The plural light beams may be provided by using plural light sources or by using a suitable beam splitter for dividing a single light beam from a source into plural light beams. Also, a single light beam after being scanningly deflected by suitable deflecting means such as a polygonal mirror, may be divided. Where plural light beams are used, plural and discrete detecting means are preferably provided in accordance with the present invention.

Figure 5:
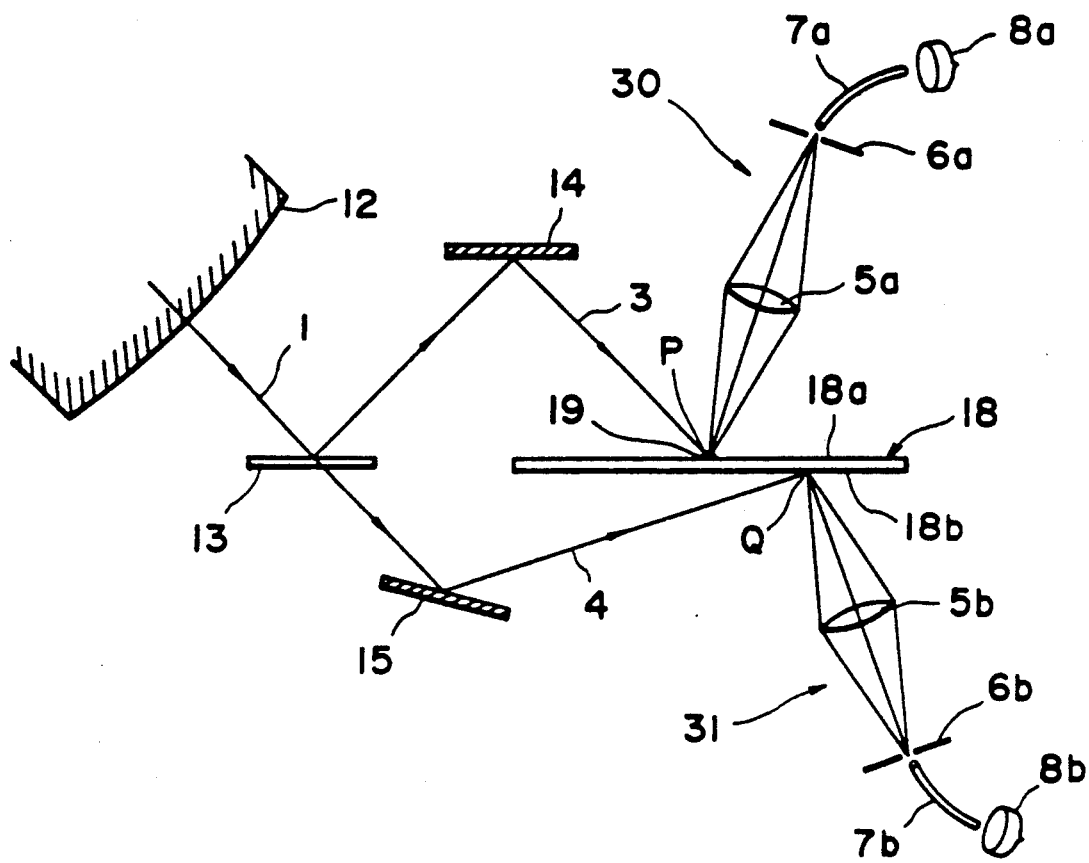
FIG. 5 is a schematic view showing an optical arrangement of a major portion of a surface examining apparatus according to another embodiment of the present invention.

Referring now to FIG. 5, there is shown an optical arrangement of a major portion of a surface examining apparatus according to another embodiment of the present invention.

In FIG. 5, a reticle 18 is held by a reticle supporting stage, not shown, with its pattern bearing surface 18b facing down and with its non-pattern bearing surface 18a facing up. Disposed above the reticle 18 are a reflecting mirror 14 for illuminating the upper surface (non-pattern bearing surface) of the reticle 18 and a light-receiving system 30 for examining the upper surface 18a of the reticle 18. The system 30 comprises a light-collecting lens 5a, a field stop (or slit-plate) 6a, an optical fiber means 7a, a photosensor 8a such as a semiconductor photoreceptor, a photomultiplier, or the like, and other elements. Similarly, disposed below the reticle 18 are a reflecting mirror 15 for illuminating the lower surface (pattern bearing surface) 18b of the reticle 18 and a light-receiving system 31 for examining the lower surface of the reticle. The system 31 is similar to the system 30, and comprises a light-collecting lens 5b, a field stop (or slit-plate) 6b, an optical fiber means 7b, a photosensor 8b and other elements. The apparatus further includes a scanning optical system 12 comprising a rotatable mirror, not shown, and other elements. A light beam from a laser source, not shown, is incident on the scanning optical system 12 and is scanningly deflected thereby, such that a scanning light beam denoted at 1 in FIG. 5 is produced. By this scanning light beam 1, the reticle 18 surfaces are scanned in the direction perpendicular to the sheet of the drawing. On the optical path of the light beam 1 from the scanning optical system 12, a half mirror 13 is provided. By this mirror 13, the scanning light beam 1 is divided into two, the two split light beams impinging on the upper and lower surfaces 18a and 18b of the reticle 18 simultaneously by way of the mirrors 14 and 15. At this time, the point P of irradiation on the upper surface 18a and the point Q of irradiation on the lower surface 18b, are shifted or deviated from each other with respect to the horizontal direction as viewed in FIG. 5. That is, the half mirror 13 and the mirrors 14 and 15 are so arranged that the light beams 3 and 4 are incident, at one time, on different and spaced positions on the reticle 18. Also, the optical path lengths for the scanning beams 3 and 4 are so determined that these beams are focused upon the respective surfaces to be examined. In this case, the mirrors 13–15 are arranged so that the same optical path length is defined for the scanning beams 3 and 4.

For the surface examination of the reticle 18, the scanning light beam 1 from the scanning optical system 12 is divided by the half mirror 13 into two light beams 3 and 4 which are incident on the upper and lower surfaces 18a and 18b of the reticle 18, simultaneously with each other, and at points P and Q spaced by a suitable distance with respect to the horizontal direction as viewed in FIG. 5. By these light beams 3 and 4, the reticle 18 surfaces are scanned in the direction perpendicular to the sheet of the drawing. If a particle 19 is deposited at the point P, the light beam 3 irradiating the particle 19 is reflected irregularly by the particle 19, such that scattered light rays advance isotropically or in substantially all directions from the point P. A portion of the scattered light rays is collected by the collecting lens 5a and passes through the stop 6a. The light passed through the stop 6a is directed by the fiber means 7a to the photosensor 8a, whereby it is photoelectrically detected. The stops 6a and 6b of the systems 30 and 31 are disposed respectively in the vicinity of point of concentration defined by the collecting lenses 5a and 5b, respectively. Therefore, each of the light-receiving systems 30 and 31 receives only the light scatteringly reflected from a corresponding one of the surfaces of the reticle being scanned by a corresponding one of the scanning beams 3 and 4, and does not receive the scattered light rays caused by the other scanning beam 4 or 3. Accordingly, the light scatteringly reflected from the particle 19 is not detected by the photosensor 8b of the system 31 provided on the opposite side.

Figure 6:
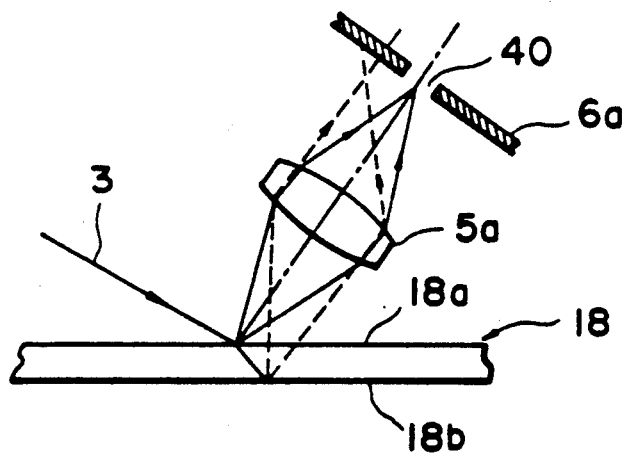
FIG. 6 is a schematic view illustrating the function of an optical field stop means included in the arrangement of FIG. 5.

The function of the stops 6a and 6b will be described in more detail, taken in conjunction with FIG. 6. A portion of the scanning beam 3 irradiating the upper surface 18a of the reticle 18 is scatteringly reflected by this surface of the reticle 18. As depicted by solid lines, a portion of the scattered light rays is collected and converged by the collecting lens 5a to a point near a slit 40 of the stop 6a, and passes through the slit 40. On the other hand, the remaining portion of the beam 3, not scattered, is transmitted through the reticle 18 and is scatteringly reflected by the circuit pattern, not shown, or foreign particles on the pattern bearing surface 18b which is on the opposite side. A portion of the thus scattered light rays is collected by the collecting lens 5a as depicted by broken lines. However, these scattered light rays (broken lines) from the pattern bearing surface 18b are converged toward a point remote from the slit 40 of the stop 6a, with the result that they are intercepted by the stop 6a and are not detected by the photosensor 8a. In this manner, the direction of projection of the scanning beam 3 and the optical axis of the light-receiving system 30 (a dash-and-dot line in FIG. 6) are determined so as to define a predetermined angle therebetween. Also, the focal point of the collecting lens, the size and the position of the slit of the stop, and so on are predetermined suitably. This is also the case with the light-receiving system 31 on the opposite side. As a matter of course, the collecting lenses 5a and 5b are positioned so that non-scattered light, being transmitted through or specularly reflected by the reticle 1, is not incident thereon.

Figure 7:
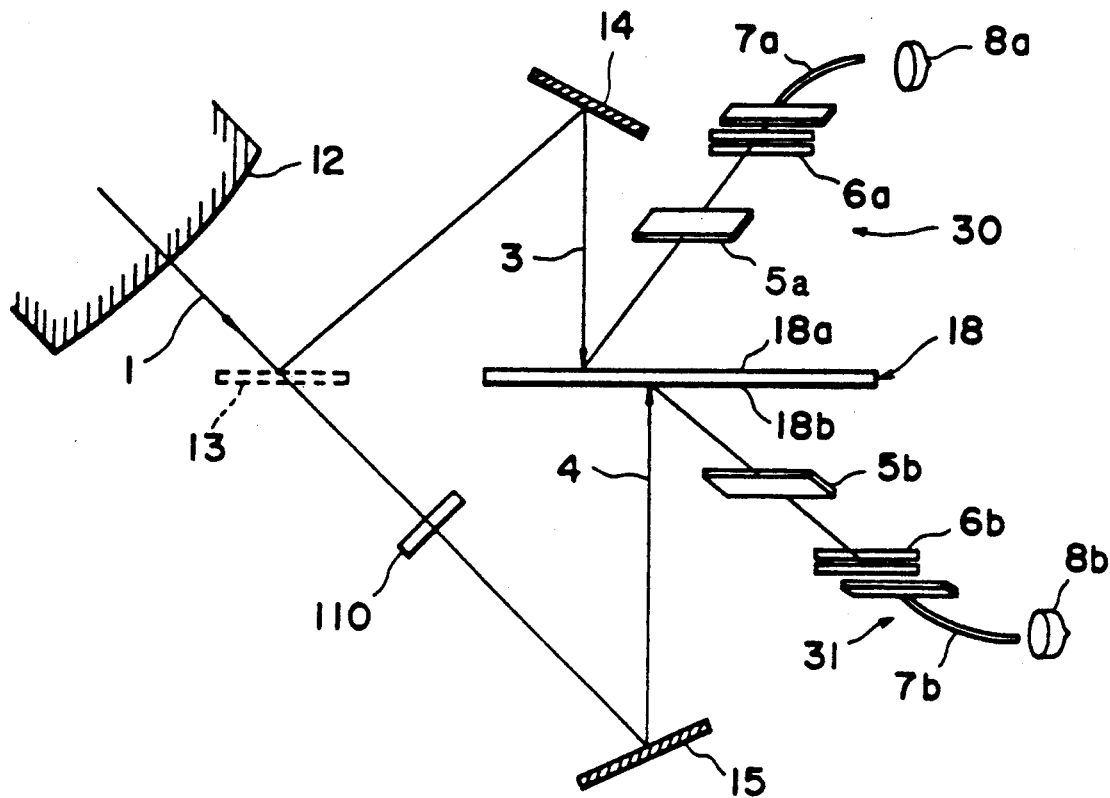
FIG. 7 is a schematic view showing a modified form of the surface examining apparatus shown in FIG. 5.

FIG. 7 shows an optical arrangement of a modified form of the examining apparatus shown in FIG. 5. In the example of FIG. 7, the light beam 1 is divided by the half mirror 13 into scanning beams 3 and 4 which are perpendicularly incident on the opposite surfaces of the reticle 18 by means of the mirrors 14 and 15. In order that the same optical distance, to the reticle 18 surface, is defined for both the beams 3 and 4 such that they are focused upon the upper and lower surfaces of the reticle 18, respectively, there is provided a transparent flat parallel-plate member 110 which is disposed between the half mirror 13 and the mirror 15. Further, the collecting lens 5a or 5b of each light-receiving system 30 or 31 is provided by an array of gradient-index type lens elements such as Selfoc lenses (Trade Name). This is effective to make the light-receiving system compact. The array of gradient-index type lens elements may be replaced by a cylindrical lens system or an array of bar lenses. The remaining portion of the arrangement of FIG. 7 is substantially the same as the corresponding portion of the FIG. 5 embodiment.

Figure 8:
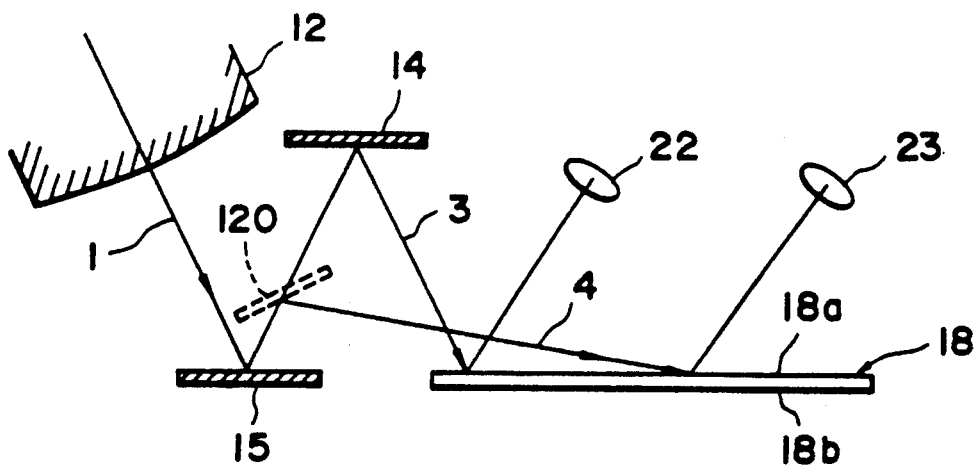
FIG. 8 is a fragmentary and schematic view showing a modified form of the examining apparatus shown in FIG. 5.

FIG. 8 shows another example. In this example, a half mirror 120 is provided between two mirrors 14 and 15 such that the same surface (non-pattern bearing surface 18a in this example) of the reticle 18 is scanned with two scanning beams 3 and 4 at the same time. The half mirror 120 and the mirrors 14 and 15 are so positioned that the same optical path length is defined for the split scanning beams 3 and 4. Denoted at 22 and 23 are light-receiving systems which are provided in association with the two scanning beams, respectively. Each of these systems 22 and 23 has substantially the same structure as the corresponding portion of the embodiment shown in FIGS. 5 or 7.

Figure 9:
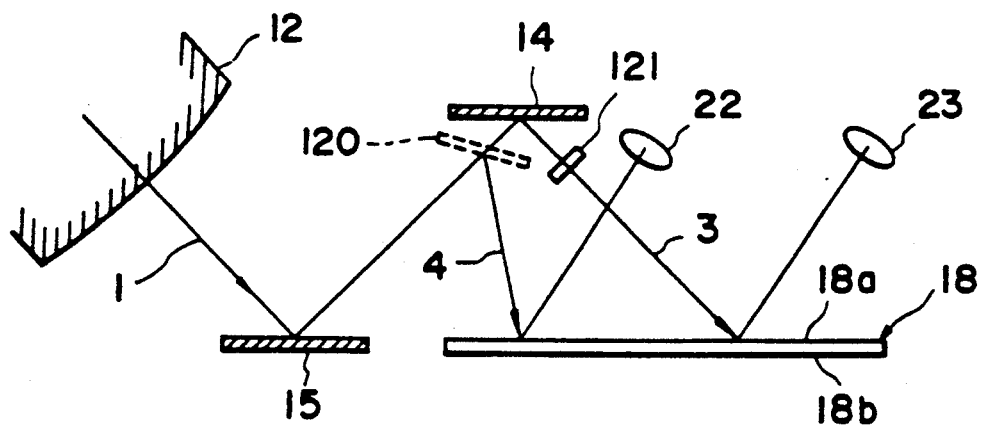
FIG. 9 is a view similar to FIG. 8 but showing a further modified form of the examining apparatus of FIG. 5.

FIG. 9 shows a modified form of the FIG. 8 example. In the FIG. 9 example, a transparent flat parallel-plate member 121 is provided as the means for correcting the optical path length for the two scanning beams 3 and 4, as in the case of the FIG. 7 embodiment. Except for this point, the arrangement of this example is the same as the FIG. 8 example.

It is to be noted that the angle of irradiation (or angle of incidence) of each scanning beam to the surface being examined, the distance between the points of irradiation (or points of incidence) of the two scanning beams 3 and 4 (with respect to the horizontal direction as viewed in the drawings), and so on can be adjusted by changing the position and/or the attitude of the half mirror, full mirrors, the parallel-plate member, etc. Also, a prism member may be used in place of the parallel-plate member so as to correct the optical path length. Where such prism member is used, the angle of irradiation (angle of incidence) can be controlled thereby.

Figure 10:
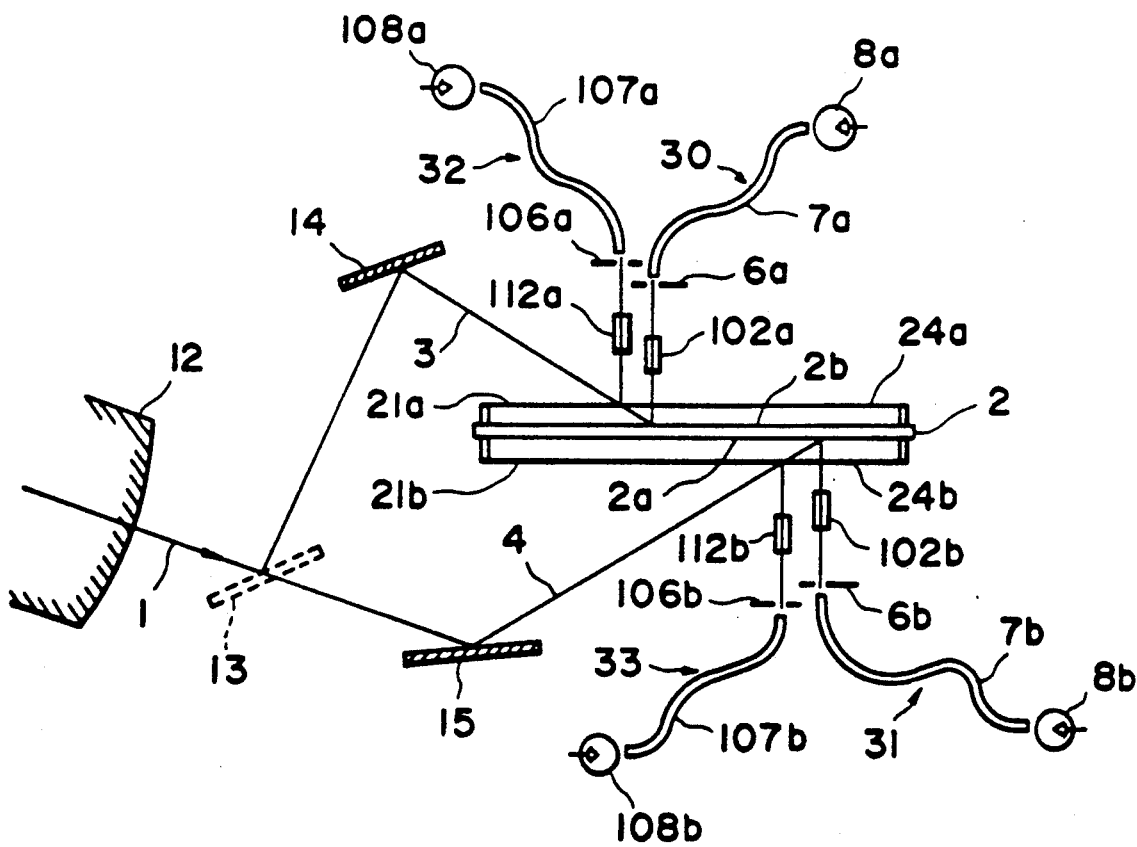
FIG. 10 is a schematic view showing an optical arrangement of a developed form of the examining apparatus shown in FIG. 5.

FIG. 10 shows an optical arrangement of a major portion of a surface examining apparatus according to a further embodiment of the present invention. In this embodiment, the present invention is applied to an examining apparatus for examining a reticle with pellicle protecting films and for detecting the presence or absence of any foreign particles adhered to four surfaces.

As shown in FIG. 10, the reticle denoted at 2 has a pattern bearing surface 2a and a non-pattern bearing surface 2b, these surfaces being protected by pellicle protecting films 24b and 24a, respectively. Thus, in this example, the surfaces 2a and 2b of the reticle 2 and upper and lower surfaces 21a and 21b of the pellicle protecting films 24a and 24b are the "surfaces to be examined". Split scanning beams 3 and 4 are projected upon the reticle surfaces 2b and 2a. Also, reflected light from the pellicle surfaces 21a and 21b are detected thereby to examine the same. For this purpose, the examining apparatus is provided with two light-receiving systems 30 and 31 for the examination of the reticle surfaces and, in addition thereto, two light-receiving systems 32 and 33 are provided for the examination of the pellicle surfaces. The four light-receiving systems 30–33 have the same structure and include, respectively, light-collecting lens-arrays 102a, 102b, 112a and 112b; field stops (slit-plates) 6a, 6b, 106a and 106b; optical-fiber bundles 7a, 7b, 107a and 107b; and photosensors 8a, 8b, 108a and 108b. By suitably arranging and disposing the field stops (6a, 106a; 6b, 106b) of the four light-receiving systems, interference or mutual disturbance of the scattered light rays, to be received by adjacent light-receiving systems (30 and 32; or 31 and 33) can be effectively prevented, whereby undesirable "crosstalk" between adjacent light-receiving systems is avoided. Therefore, the existence of any foreign particle can be detected accurately. Further, it is possible to discriminate the surface that bears the foreign particle.

In accordance with the embodiments having been described with reference to FIGS. 5–10, plural beams are projected upon plural surfaces and at points which are spaced with respect to the direction parallel to the surfaces being examined. This provides the following advantageous effects:

(1) Simultaneous irradiation of the plural surfaces with the plural scanning beams reduces the time necessary for the examination.
(2) The shift of irradiation points on the plural surfaces, described above, ensures easy and exact discrimination of the surface on which the foreign particles are adhered. Therefore, the reliability of the examination is improved extraordinarily.
(3) It is not necessary to use a specific mechanism for sequentially shifting the focus for the individual surfaces. Further, use of a lens array, such as an array of gradient-index type lens elements, in the light-receiving system makes it possible to reduce the size of the examining apparatus.
(4) The plural-beam scanning of the same surface, as in the embodiments of FIGS. 8 and 9, reduces the amount of movement of the subject of examination. That is, where two scanning beams are used for the examination of the same surface, approximately only half the length of the subject of examination (the surface to be examined) is necessary for the amount of movement of the subject. Accordingly, the time for the examination can be reduced and the structure of the apparatus can be made compact.

The number of the scanning beams to be used for the examination is not limited to "two", and three or more scanning beams may of course be used. Where a single beam is used as in the FIG. 3 embodiment, however, the optical arrangement can be made simple and compact and, additionally, the light from the light source can be utilized more efficiently.

As for the relative movement of the subject of examination with respect to the examining optical system, for the purpose of whole-surface examination, the subject of examination may be moved translationally or rotationally. It is a possible alternative to scanningly deflect one or more light beams two-dimensionally. Further, in place of scanningly deflecting the light beam, the subject of examination itself may be moved two-dimensionally.

Figure 11A:
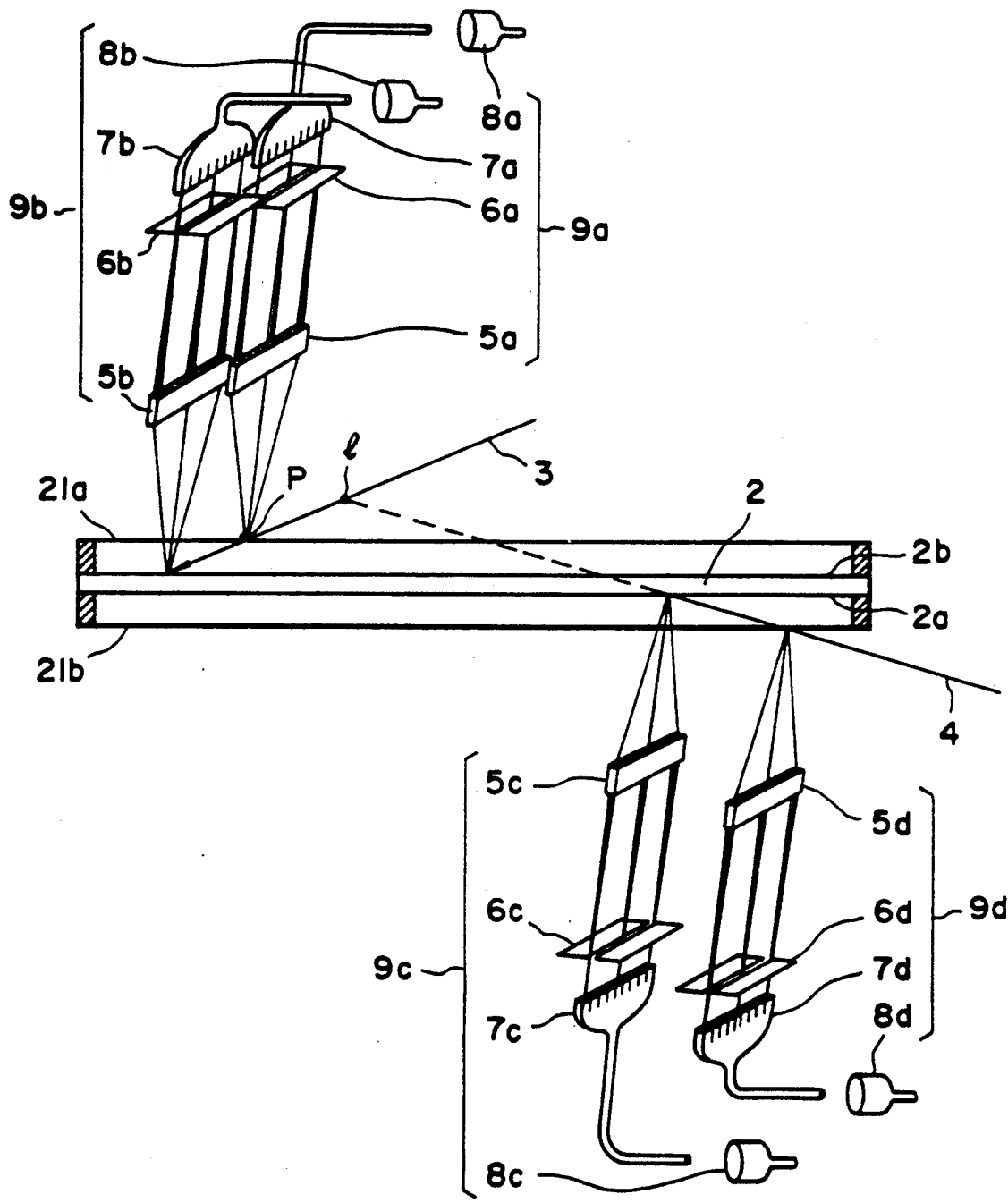
FIG. 11A is a schematic view showing an optical arrangement of a major portion of a surface examining apparatus according to a further embodiment of the present invention.
Figure 11B:
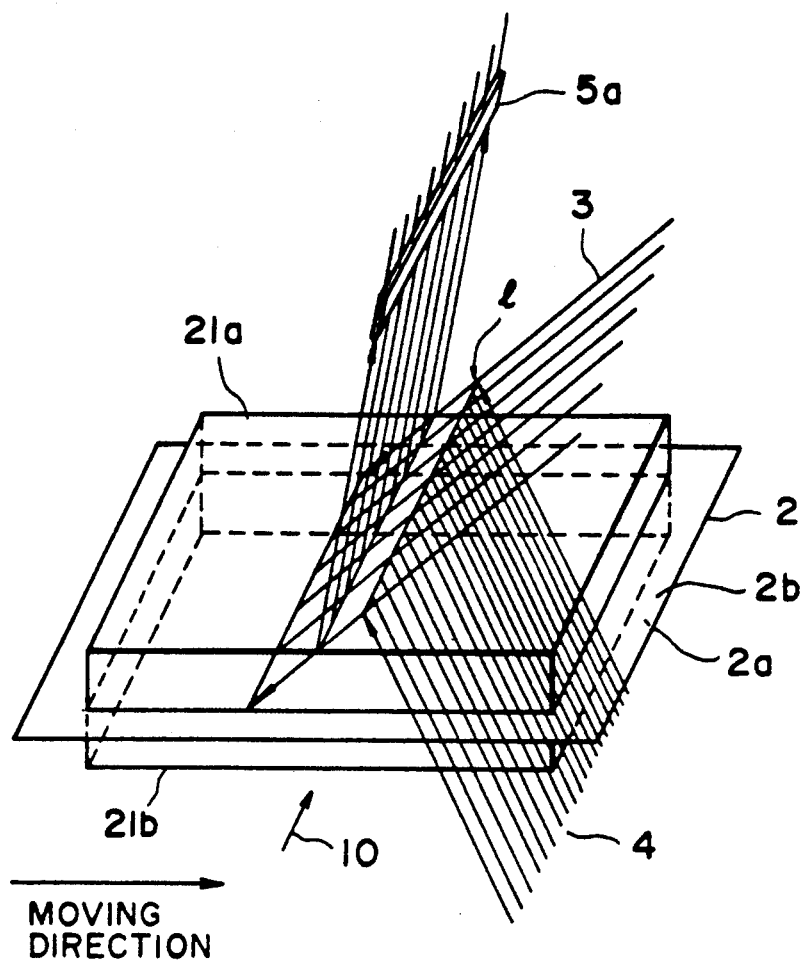
FIGS. 11B and 11C are schematic views, respectively, for explaining the manner of projection of scanning light beams upon plural surfaces, in the examining apparatus of FIG. 11A.
Figure 11C:
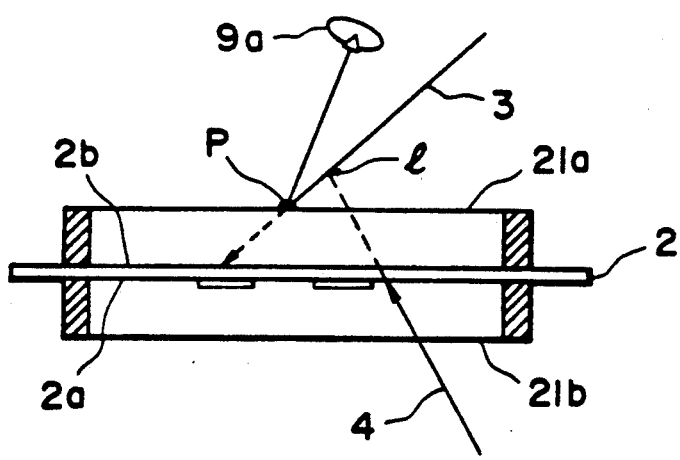

Referring now to FIGS. 11A-11C, description will be made to a surface examining apparatus according to a still further embodiment of the present invention.

In this embodiment, as illustrated, a reticle 2 having a pattern bearing surface 2a and a non-pattern bearing surface 2b is covered by pellicle protecting films 21b and 21a. A light beam from a light source such as a laser source, not shown, is scanningly deflected by a suitable scanning means such as a polygonal mirror, also not shown, and then is divided by a suitable beam splitting means, not shown, such that two scanning light beams 3 and 4 are produced. The scanning beam 3 is projected upon the upper pellicle surface 21a and the non-pattern bearing surface 2b of the reticle 2, while the scanning beam 4 is projected upon the lower pellicle surface 21b and the pattern bearing surface 2a of the reticle 2. Also, the scanning beams 3 and 4 are effective to scan these surfaces in the direction perpendicular to the sheet of the drawing. Optical members 5a-5d each comprise a plurality of gradient-index type minute lens elements which are disposed in an array extending one-dimensionally. The optical members 5a-5d have been adjusted so as to be focused upon the surfaces 21a, 2b, 2a and 21b, respectively. Field stops (or slit-plates) 6a-6d are disposed respectively in the vicinity of the positions that are optically conjugate with the surfaces 21a, 2b, 2a and 21b, respectively, with respect to the optical members 5a-5d, respectively. Four light-guides 7a-7d are provided so as to guidingly direct the light, passed through the field stops 6a-6d, toward four photodetectors 8a-8d, respectively.

In the present embodiment, the optical member 5a, the field stop 6a, the light-guide 7a and the photodetector 8a are cooperative with each other and constitute a portion of a first detecting means denoted at 9a. Similarly, the remaining optical members 5b-5d, the field stops 6b-6d, the light-guides 7b-7d and the photodetectors 8b-8d cooperate to provide portions of second, third and fourth discrete detecting means 9b, 9c and 9d, respectively.

While two light beams are used to examine the four surfaces 21a, 2b, 2a and 21b, four light beams may of course be used to examine the four surfaces, respectively.

FIG. 11B is a perspective view of a portion of the arrangement shown in FIG. 11A, and illustrates the manner of irradiation of the scanning beams 3 and 4 upon the surfaces being examined. FIG. 11C is a schematic view corresponding to FIG. 11B, as seen in the direction of arrow 10 in FIG. 11B.

An important feature of the present invention is that, as best seen in FIGS. 11B and 11C, the plural scanning beams such as at 3 and 4 are so projected that one or more lines of intersection (denoted at l), between planes (scan planes) each defined by one light beam scanningly deflected so as to scan one of the surfaces being examined, do not intersect with or coincide with any one of the surfaces being examined.

In the example of FIG. 11A, the light beam 3 is used to scan the upper pellicle surface 21a and the upper surface 2b of the reticle 2. Accordingly, one and the same plane is defined by the scanning light beam that examines the surfaces 21a and 2b. Similarly, the light beam 4 is used to scan the lower pellicle surface 21b and the lower surface 2a of the reticle 2. Therefore, one and the same plane is defined by the light beam that examines the surfaces 21b and 2a. Consequently, in the present embodiment, two planes (scan planes) are defined by the scanning beams. As a matter of course, where four light beams are used, four planes will be defined. In the present embodiment, as is best seen in FIG. 11C, the scanning beams 3 and 4 are so projected that the line of intersection (l), which is single in this case, does not intersect or coincide with any one of the plural surfaces being examined.

Details of the examining operation of the present embodiment will now be described, taken in conjunction with FIGS. 11A-11C.

If a particle P is adhered to the surface 21a and when the light beam 3 is incident on this particle P, the light beam 3 is scatteringly reflected by the particle P isotropically or non-directionally. Since, in this case, the first detecting means 9a is focused upon the surface 21a, the optical member 5a of the first detecting means can collect the scattered light rays very efficiently. As a result, the photodetector 8a produces an output of increased level. On the other hand, the second, third and fourth detecting means 9b, 9c and 9d are defocused with respect to the surface 21a. Moreover, in the vicinity of the positions which are optically conjugate respectively with the surfaces 2b, 2a and 21b with respect to the optical members 5b, 5c and 5d of these detecting means, the field stops 6b, 6c and 6d are disposed, respectively, as described hereinbefore. Accordingly, the scattered light rays from the particle P on the surface 21a are sufficiently intercepted by means of the field stops 6b, 6c and 6d. As a result, the outputs of the photodetectors 8b, 8c and 8d are maintained substantially constant. Thus, by monitoring the output of the photodetector 8a, the particle P can be detected during the examination of the surface 21a.

In the present embodiment, as will be understood from the foregoing, the presence or absence of any foreign particles on the four surfaces is detected discriminately, on the basis of the output signals from the four photodetectors 8a-8d. Further, in the present embodiment, the size or magnitude of any foreign particle is discriminated by detecting the magnitude of an output or the level of an output signal from a corresponding one of the photodetectors 8a-8d. The manner of such magnitude detection is known per se.

The simultaneous projection of plural beams upon plural points on plural surfaces, together with use of plural and discrete detecting means, in the present embodiment allows high-accuracy and high-speed detection of any foreign particle. Also, it enables discrimination of the surface that bears the foreign particle.

Figures 12A, 12B:
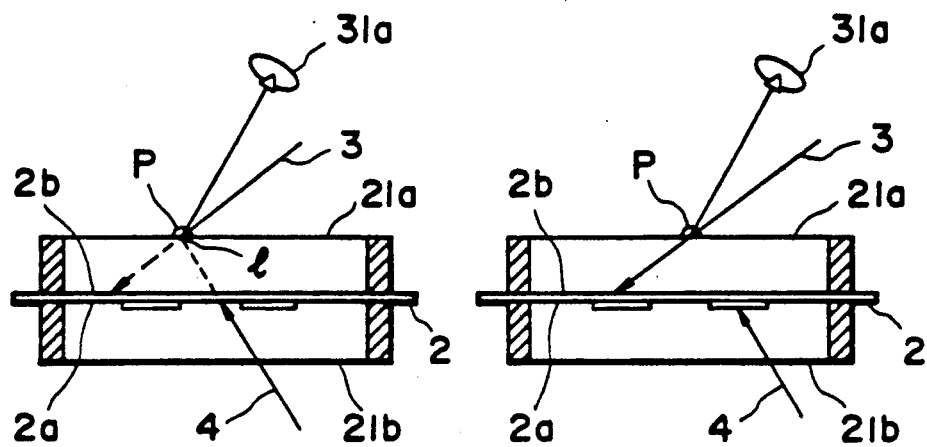
FIGS. 12A and 12B are schematic views, respectively, illustrating an inconvenience, in comparison with advantageous effects of the examining apparatus shown in FIG. 11A.

The advantageous effects of the present embodiment will be more readily understood from FIGS. 12A and 12B. In the case of FIG. 12A, the light beam 3 is used to scan the upper pellicle surface 21a and the upper surface 2b of the reticle, while the light beam 4 is used to scan the lower pellicle surface 21b and the lower surface 2a of the reticle. This is the same as the FIG. 11A embodiment. Similarly, detecting means 31a is provided to detect the scattered light rays from the upper pellicle surface 21a. However, as compared with the FIG. 11A embodiment, the line of intersection (l), between two planes defined by the light beam 3 scanningly deflected to scan the upper pellicle surface 21a and by the light beam 4 scanningly deflected to scan the reticle surface 2a, does intersect or coincide with the upper pellicle surface 21a which is one of the surfaces being examined. If the reticle 2 is at the position, shown in FIG. 12A, relative to the examining optical system, the light beam 4 from below is incident on the upper pellicle surface 21a. If, on the other hand, the reticle 2 is moved to the position shown in FIG. 12B, the light beam 4 will be blocked by the circuit pattern made of Cr or $CrO_2$ or, alternatively, by foreign particles on the reticle 2. Thus, during movement of the reticle 2 relative to the examining optical system, there occurs variation in the quantity of light irradiating the upper pellicle surface 21a. In other words, there occurs varying illuminance on the upper pellicle surface 21a, the illuminance varying between the FIG. 12A case and the FIG. 12B case.

Usually, the intensity of light scattered by a particle adhered to a surface being examined is proportional to the size or magnitude of the particle. For this reason, by detecting the magnitude or level of an output signal from corresponding detecting means, the size of the particle can be detected or discriminated with a certain accuracy. If, however, the illuminance on the surface being examined varies as in the cases of FIGS. 12A and 12B, the output signals of the same detecting means which are produced in response to irradiation of foreign particles of the same size will not have the same level, the differences in level being dependent upon the differences in position of the particles. Therefore, it is difficult to accurately discriminate the size of the particle.

In the present embodiment, as described hereinbefore and as best seen in FIG. 11C, the line of intersection, between plural planes each defined by one light beam scanningly deflected so as to scan one of the surfaces being examined, does not intersect with or coincide with any one of the surfaces being examined. With such an arrangement, undesirable variation in illuminance upon a surface to be examined can be effectively avoided and, therefore, discrimination of the size of the particle as well as the discrimination of the surface that bears the particle can be attained stably.

Figure 13:
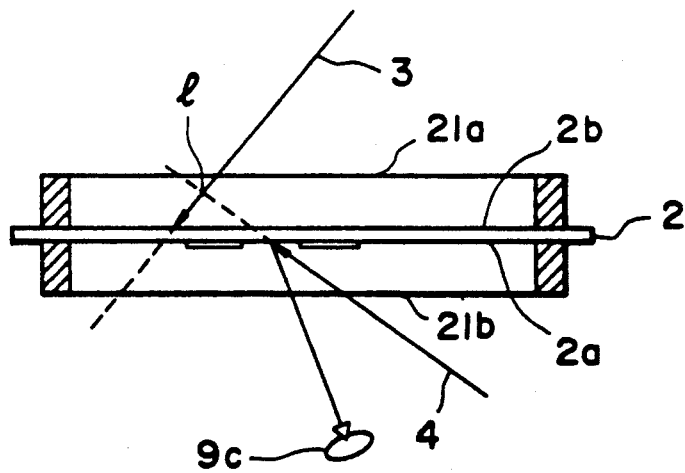
FIGS. 13-16 are fragmentary views, respectively, schematically showing modified forms of the examining apparatus shown in FIG. 11A.
Figure 14:
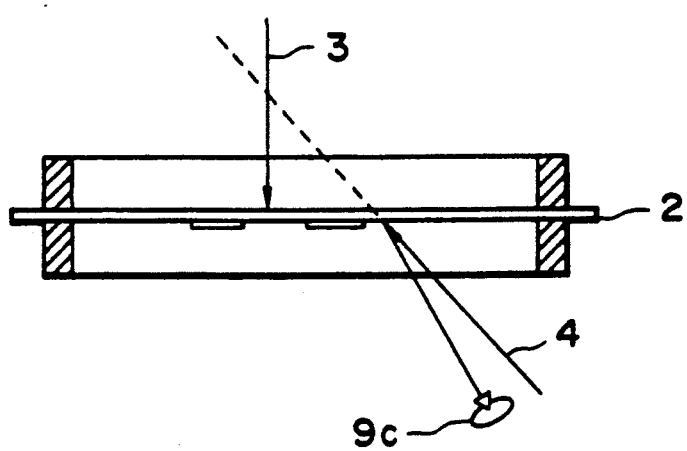
Figure 15:
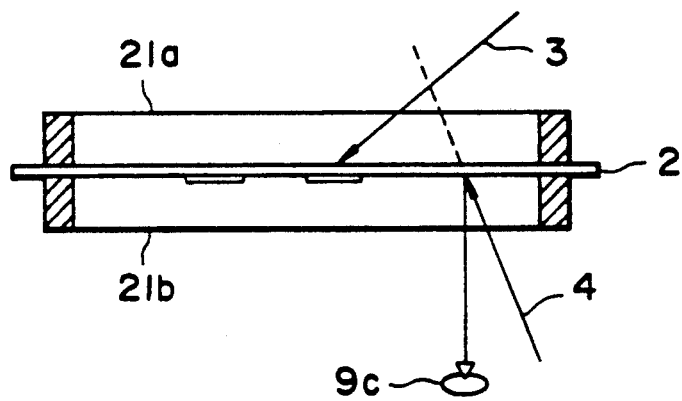
Figure 16:
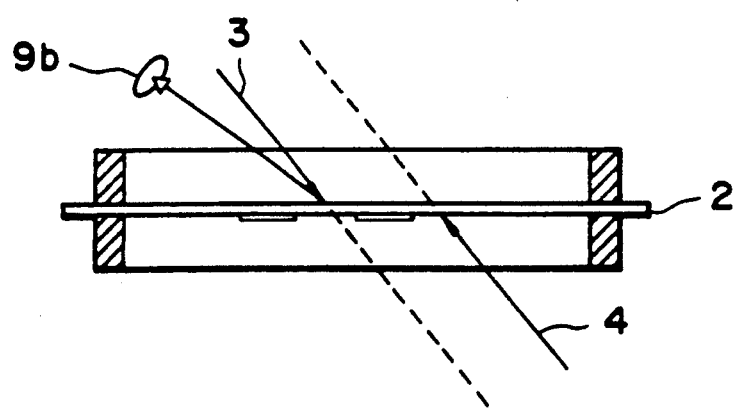

FIGS. 13-16 are views similar to FIG. 11C and show modified forms of the examining apparatus of the embodiment described with reference to FIGS. 11A-11C. In the example of FIG. 13, a plane which is defined by a light beam 3 scanningly deflected to scan surfaces 21a and 2b and a plane which is defined by a light beam 4 scanningly deflected to scan surfaces 21b and 2a, intersect along a line l that is between the upper pellicle surface 21a and the upper surface 2b of the reticle 2. In the case of FIG. 14, one (3) of two light beams is perpendicularly incident on the reticle 2. In the case of FIG. 15, a light beam 4 is incident at an incline on the reticle 2, while detecting means 9c is disposed so as to receive a portion of the scatteringly reflected light from the reticle 2 that advances substantially perpendicularly to the reticle 2. In the case of FIG. 16, two light beams 3 and 4 are projected upon upper and lower pellicle surfaces along parallel paths.

In each of the FIGS. 13-16 examples, the above-described line of intersection denoted at l does not coincide with any one of the surfaces being examined.

In accordance with the embodiments described with reference to FIGS. 11A-11C and 13-16, the examining apparatus is arranged so that one or more lines of intersection, between planes each defined by one light beam scanningly deflected so as to scan one of surfaces being examined, do not intersect or coincide with any one of the surfaces being examined. With this arrangement, the surface on which a foreign particle is deposited can be detected very accurately and in a reduced time. Further, the size of the particle can be discriminated accurately and at the same time.

Figure 17A:
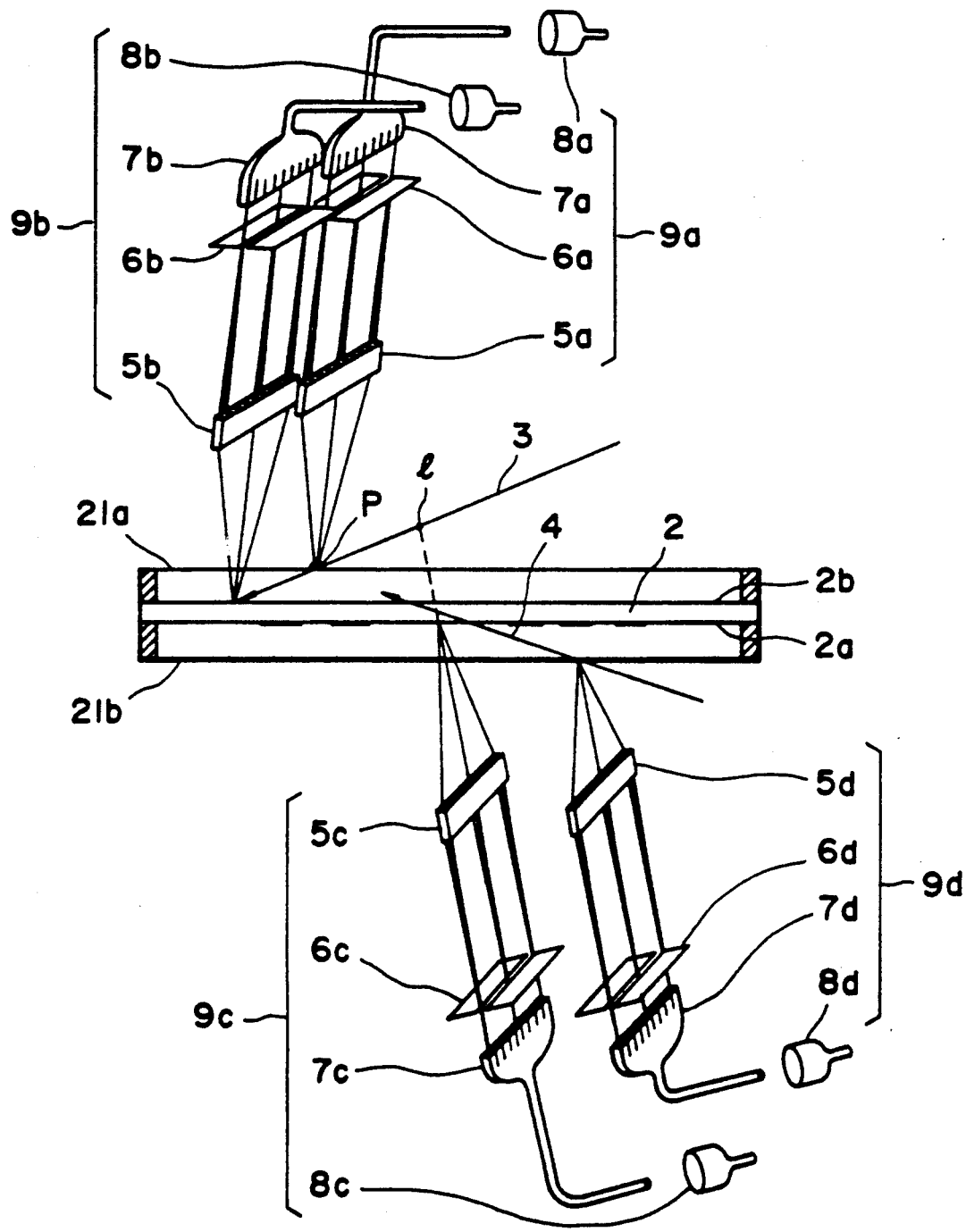
FIG. 17A is a schematic view showing an optical arrangement of a major portion of a surface examining apparatus according to a still further embodiment of the present invention.
Figure 17B:
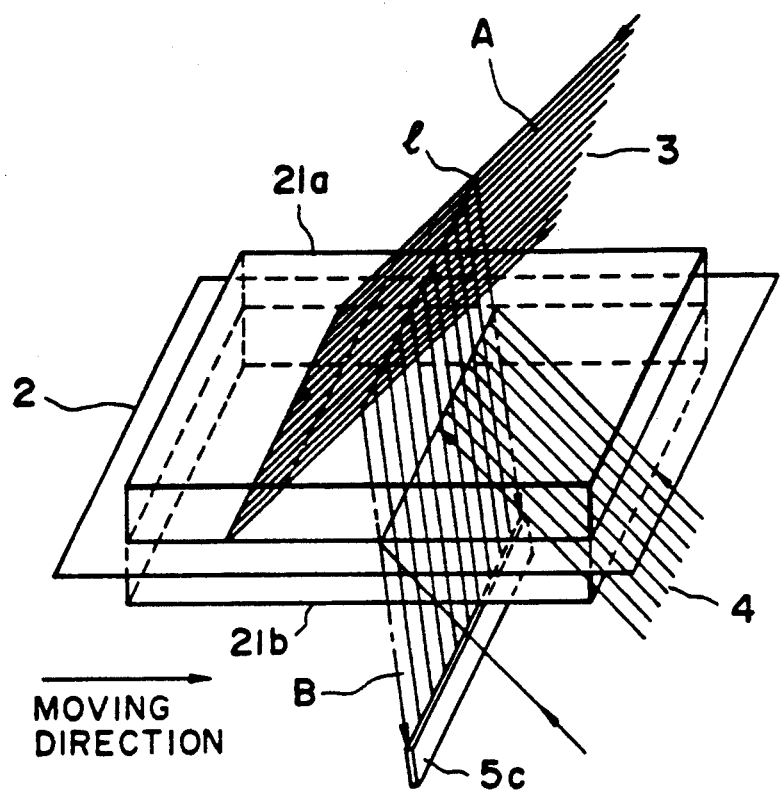
FIGS. 17B and 17C are schematic views, respectively, showing the manner of projection of scanning light beams upon plural surfaces, in the examining apparatus of FIG. 17A.
Figure 17C:
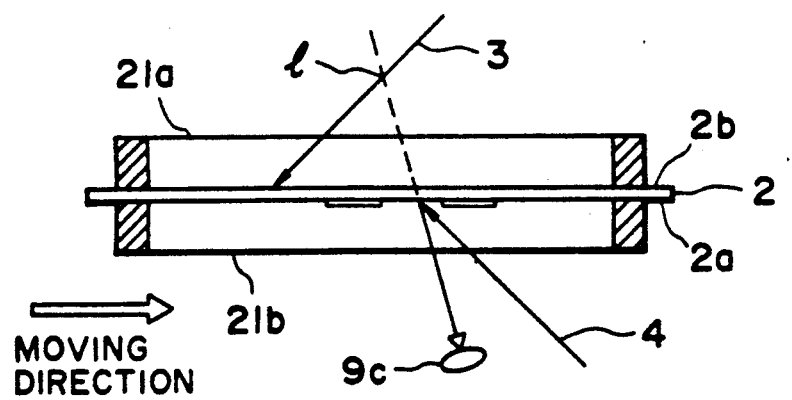

Referring now to FIGS. 17A-17C, description will be made to a surface examining apparatus according to yet another embodiment of the present invention.

In this embodiment, as illustrated, a reticle 2 having a pattern bearing surface 2a and a non-pattern bearing surface 2b is covered by pellicle protecting films 21b and 21a. A light beam from a light source such as a laser source, not shown, is scanningly deflected by a suitable scanning means such as a polygonal mirror, also not shown, and then is divided by a suitable beam splitting means, not shown, such that two scanning light beams 3 and 4 are produced. The scanning beam 3 is projected upon the upper pellicle surface 21a and the non-pattern bearing surface 2b of the reticle 2, while the scanning beam 4 is projected upon the lower pellicle surface 21b and the pattern bearing surface 2a of the reticle 2. Also, the scanning beams 3 and 4 are effective to scan these surfaces in the direction perpendicular to the sheet of the drawing. Optical members 5a-5d each comprise a plurality of gradient-index type minute lens elements which are disposed in an array extending one-dimensionally. The optical members 5a-5d have been adjusted so as to be focused upon the surfaces 21a, 2b, 2a and 21b, respectively. Field stops (or slit-plates) 6a-6d are disposed respectively in the vicinity of the positions that are optically conjugate with the surfaces 21a, 2b, 2a and 21b, respectively, with respect to the optical members 5a-5d, respectively. Four light-guides 7a-7d are provided so as to guidingly direct the lights, passed through the field stops 6a-6d, toward four photodetectors 8a-8d, respectively.

In the present embodiment, the optical member 5a, the field stop 6a, the light-guide 7a and the photodetector 8a are cooperative with each other and constitute a portion of a first detecting means denoted at 9a. Similarly, the remaining optical members 5b-5d, the field stops 6b-6d, the light-guides 7b-7d and the photodetectors 8b-8d cooperate to provide portions of second, third and fourth discrete detecting means 9b, 9c and 9d, respectively.

While two light beams are used to examine the four surfaces 21a, 2b, 2a and 21b, four light beams may of course be used to examine the four surfaces, respectively.

FIG. 17B is a perspective view of a portion of the arrangement shown in FIG. 17A, and illustrates the manner of irradiation of the scanning beams 3 and 4 upon the surfaces being examined. FIG. 17C is a schematic view corresponding to FIG. 17B, as seen in the direction of arrow 10 in FIG. 17B.

An important feature of the present embodiment lies in that, as best seen in FIGS. 17B and 17C, the line of intersection between (i) a plane (scan plane) defined by one light beam scanningly deflected so as to scan a corresponding one of the plural surfaces being examined and (ii) a plane including the axis or axes of any one of the plural detecting means, other than the detecting means that is used in association with the examination of the aforesaid one surface, does not intersect or lie on any one of the plural surfaces. In the particular example of FIGS. 17B and 17C, the light beam 3, when it is scanningly deflected to scan the surface 21a, defines a plane A. On the other hand, the optical axes of the lens elements of the optical member 5c, which is a component of the third detecting means 9c (FIG. 17A) that is used for the examination of the surface 2a rather than the surface 21a, are included in a plane B. As shown in FIGS. 17B and 17C, the planes A and B intersect along a line l. And, the line of intersection (l) does not intersect or lie on any one of the plural surfaces being examined.

The plural scanning beams are projected and the plural detecting means are disposed, both in the manner that satisfies the above-described relation. While, in FIGS. 17B and 17C, only the optical member 5c and the detecting means 9c are illustrated, the remaining optical members 5a, 5b and 5d and the remaining detecting means 9a, 9b and 9d are all so disposed as to satisfy the above-described relation.

In the example of FIG. 17A, the light beam 3 is used to scan the upper pellicle surface 21a and the upper surface 2b of the reticle 2. Accordingly, one and the same plane denoted at A is defined by the scanning light beam that examines the surfaces 21a and 2b. Similarly, the light beam 4 is used to scan the lower pellicle surface 21b and the lower surface 2a of the reticle 2. Therefore, one and the same plane is defined by the light beam that examines the surfaces 21b and 2a. Consequently, in the present embodiment, two planes (scan planes) are defined by the scanning beams. As a matter of course, where four light beams are used, four planes will be defined.

In the present embodiment, accordingly, the optical components are so arranged that the line l of intersection between (i) one of the two planes (e.g. A) that is defined by one light beam (e.g. 3) scanningly deflected so as to scan a corresponding one (e.g. 21a) of the plural surfaces and (ii) the plane including the optical axes of any one of the plural detecting means, other than the detecting means (e.g. 9a) that is used in association with the examination of the aforesaid one surface (e.g. 21a), does not intersect or lie on any one of the plural surfaces being examined, and, more preferably, it is located above or below the surfaces being examined. In the case of FIG. 17C, the line of intersection is defined at a position above the surface 21a. Of course, it may be defined at a position below the surfaces being examined.

Details of the examining operation of the present embodiment will be described, taken in conjunction with FIGS. 17A-17C.

If a particle P is adhered to the surface 21a and when the light beam 3 is incident on this particle P, the light beam 3 is scatteringly reflected by the particle P isotropically or non-directionally. Since, in this case, the first detecting means 9a is focused upon the surface 21a, the optical member 5a of the first detecting means can collect the scattered light rays very efficiently. As a result, the photodetector 8a produces an output of increased level. On the other hand, the second, third and fourth detecting means 9b, 9c and 9d are defocused with respect to the surface 21a. Moreover, in the vicinity of the positions which are optically conjugate respectively with the surfaces 2b, 2a and 21b with respect to the optical members 5b, 5c and 5d of these detecting means, the field stops 6b, 6c and 6d are disposed, respectively, as described hereinbefore. Accordingly, the scattered light rays from the particle P on the surface 21a are sufficiently intercepted by means of the field stops 6b, 6c and 6d. As a result, the outputs of the photodetectors 8b, 8c and 8d are maintained substantially constant. Thus, by monitoring the output of the photodetector 8a, the particle P can be detected during the examination of the surface 21a.

In the present embodiment, as will be understood from the foregoing, the presence or absence of any foreign particles on the four surfaces is detected discriminately, on the basis of the output signals from the four photodetectors 8a-8d. Further, in the present embodiment, the size or magnitude of any foreign particle is discriminated by detecting the magnitude of an output or the level of an output signal from a corresponding one of the photodetectors 8a-8d. The manner of such magnitude detection is known per se.

The simultaneous projection of plural beams upon plural points on plural surfaces, together with use of plural and discrete detecting means, in the present embodiment allows high-accuracy and high-speed detection of any foreign particle. Also, it enables discrimination of the surface that bears the foreign particle.

Figure 18A:
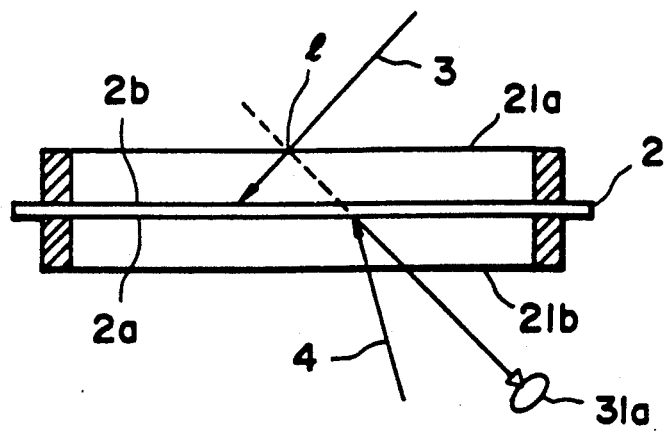
FIGS. 18A-18C are schematic views, respectively, illustrating inconveniences, in comparison with advantageous effects of the examining apparatus of FIG. 17A.
Figure 18B:
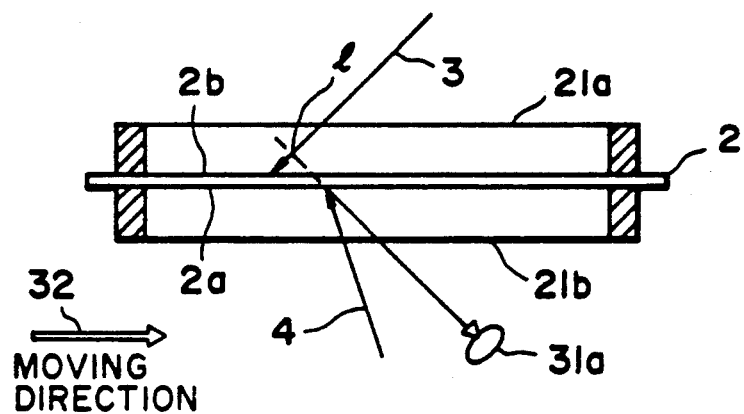
Figure 18C:
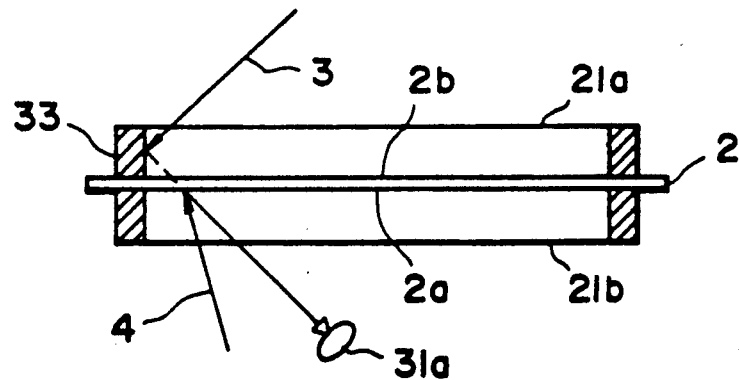

The advantageous effects of the present embodiment will be more readily understood from FIGS. 18A-18C. In the cases of FIGS. 18A and 18B, the light beam 3 is used to scan the upper pellicle surface 21a and the upper surface 2b of the reticle 2, while the light beam 4 is used to scan the lower pellicle surface 21b and the lower surface 2a of the reticle 2. This is the same as the FIG. 17C embodiment. Also, detecting means 31a is provided to detect the scatteringly reflected light from the lower surface 2a of the reticle. In these examples, however, the line l of intersection, between the plane defined by the light beam 3 scanning the surface 21a and the plane defined by the optical axis of the detecting means 31a that is provided to detect the scattered light from the surface 2a, does intersect or lie on the surface 21a (in the FIG. 18A case) which is one of the surfaces being examined. Also, in the case of FIG. 18B, the line l of intersection is defined at a position between the upper pellicle surface 21a and the upper surface 2b of the reticle. In the FIG. 18A case, it is highly possible that the detecting means 31a, provided to detect the scattered light from the surface 2a, detects the scattered light rays from particles adhered to the upper pellicle surface 21a. Therefore, it is difficult to discriminate the surface that bears the particles.

Further, there is another problem. That is, usually, the intensity of scatteringly reflected light from a particle on a surface being examined is proportional to the size or magnitude of the particle. Therefore, by detecting or measuring the magnitude or level of an output signal from detecting means, the size of the particle can be discriminated with certain accuracy. If, however, the detecting means receives scatteringly reflected light from any surface with which the aforesaid detecting means is not associated, then the detecting means does not produce an output signal of correct level that corresponds to the size of the particle. Accordingly, it is very difficult to discriminate the size of the particle accurately.

In the case of FIG. 18B, it is possible that, when the reticle 2 which is moving relative to the examining optical system reaches the position shown in FIG. 18C, the light beam 3 impinges on the pellicle frame 33 and the scatteringly reflected light rays caused thereby are detected by the detecting means 31a. In such a case, the detecting means 31 produces an output signal that represents existence of a particle.

In view of these problems, the examining apparatus of the present embodiment is arranged so that, as best seen in FIGS. 17B and 17C, the line of intersection between (i) a plane defined by one light beam scanningly deflected so as to scan a corresponding one of the plural surfaces being examined and (ii) a plane including the axis or axes of any one of the plural detecting means, other than the detecting means that is used in association with the examination of the aforesaid one surface, does not intersect or lie on any one of the plural surfaces being examined, and more preferably, does lie above or below all the surfaces being examined.

With such an arrangement, discrimination of the surface that bears a particle as well as discrimination of the size of the particle, can be attained easily and stably.

Figure 19:
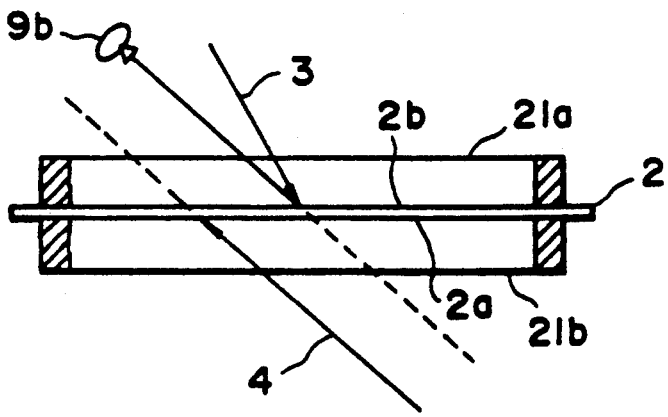
FIGS. 19-22 are fragmentary views, respectively, schematically showing modified forms of the examining apparatus shown in FIG. 17A.
Figure 20:
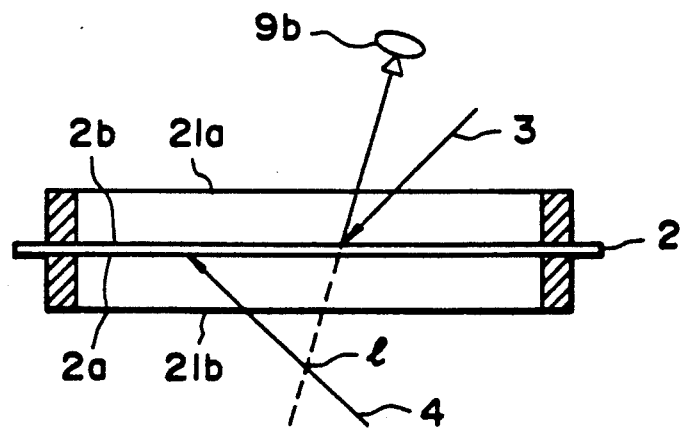

FIGS. 19-22 are views similar to FIG. 17C and show modified forms of the examining apparatus of the FIG. 17A embodiment. In the example of FIG. 19, the plane defined by a light beam 4 used to scan surfaces 2a and 21b and the plane defined by the optical axis of detecting means 9b, provided to detect the scattered light from a surface 2b, are substantially parallel to each other and, therefore, the line l of intersection of these planes is at infinity. In the example of FIG. 20, the line l of intersection, between the plane defined by a light beam 4 used to scan surfaces 21b and 2a and the plane defined by the optical axis of detecting means 9b, is defined at a position below all the surfaces being examined.

Figure 21:
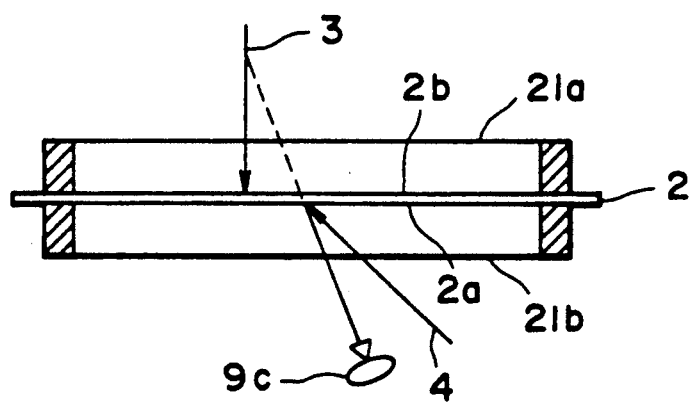
Figure 22:
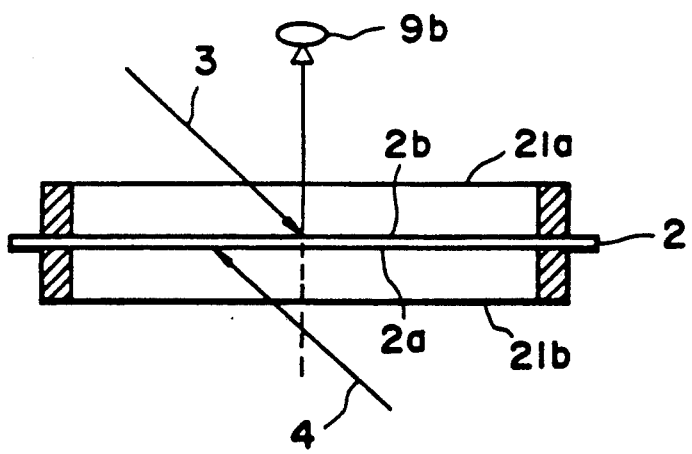

In the example of FIG. 21, one of two light beams, i.e. the light beam 3, is perpendicularly incident on the reticle 2. In the example of FIG. 22 on the other hand, the light beam 3 is incident at an incline and, in place thereof, the detecting means 9b provided in association with the examination of the surface 2b, is arranged to detect a portion of the scatteringly reflected light from the surface 2b that advances substantially perpendicularly to the reticle 2.

In each of these examples, illustrated in FIGS. 19-22, the components of the examining apparatus are so arranged that the intersection line l does not intersect or lie on any one of the plural surfaces being examined, or lie between the plural surfaces being examined.

In accordance with the embodiments having been described with reference to FIGS. 17A-17C and 19-22, the directions along which plural light beams are projected upon plural surfaces being examined and the positions of plural detecting means for detecting scattered light from the plural surfaces are determined in the specific manner as has been described hereinbefore. By this arrangement, the surface on which a particle is deposited can be discriminately detected very accurately and in a reduced time. Furthermore, the size of the particle can be discriminated accurately and at the same time.

In each of the embodiments described in the foregoing, plural surfaces are scanned with one or more light beams in the same direction. However, it is of course possible to scan these surfaces in different directions.

As for the direction along which the light beam is projected upon the subject of examination, the perpendicular projection such as disclosed, for example, in FIG. 21 is of course possible. However, inclined projection wherein the light beam is incident at an incline upon the subject of examination, such as disclosed in, e.g. FIG. 3, is preferable since it allows the optical axis of the light-receiving system to be made perpendicular to the surface being examined. Such an arrangement is advantageous which respect to ease in designing, assembling and adjusting the components of the light-receiving system.

The deflecting means for scanningly deflecting the light beam may comprise a mechanically rotating device such as a polygonal mirror, a galvano mirror, or the like. However, it may be provided by an optical deflector such as, for example, an acousto-optic device utilizing elastic waves or holograms.

Where the subject of examination is a reticle having a pair of pellicle protecting films, it is preferable to arrange the examination apparatus so that plural light beams are focused upon upper and lower surfaces of the reticle. This is because, in the field of manufacture of semiconductor devices, what should be most accurately detected is the state of each of the upper and lower surfaces of the reticle. Particularly, the most important one is the accuracy of examination of a pattern bearing surface of the reticle on which surface a circuit pattern is formed.

While the invention has been described with reference to the structures disclosed herein, it is not confined to the details set forth and this application is intended to cover such modifications or changes as may come within the purposes of the improvements or the scope of the following claims.

What is claimed is:

1. An apparatus usable with an object having a surface, for examining the state of the surface of the object, said apparatus comprising:
   light projecting means for emitting convergent light;
   light dividing means for dividing the light emitted from said light projecting means into a plurality of light beams to irradiate the object along a plurality of respective light paths at the same time, wherein the light paths of the divided light beams to points irradiated on the object have the same optical path length; and
   a plurality of light-receiving means associated with points on the surface of the object being irradiated with the plurality of light beams, said plurality of light-receiving means being arranged to receive light scatteringly reflected from the points on the surface of the object being irradiated with the light beams, each of said light receiving means comprising means for producing outputs corresponding to the state of the surface of the object at the points irradiated with the light beams.

2. An apparatus according to claim 1, wherein said light projecting means comprises a scanning optical system.

3. An apparatus for measuring the state of a surface of an object, said apparatus comprising:
   a light source for producing light;
   light dividing means for dividing the light from said light source into a plurality of light beam to irradiate the object along a plurality of respective light paths at the same time, wherein the paths of the divided light beams have the same optical path length; and
   a plurality of light receiving means comprising means for receiving light beams from respective zones on the object irradiated by the divided light beams, and means for producing outputs on the basis of which the state of surface of the object can be measured.

4. An apparatus according to claim 3, further comprising means for concurrently irradiating front and back surfaces of the object with the divided light beams.

5. An apparatus according to claim 3, further comprising means for concurrently irradiating different positions on the same surface of the object with the divided light beams.

6. An apparatus according to claim 3, wherein said light dividing means comprises a beam splitter for dividing the light from said light source into a plurality of light beams by transmission and reflection, and wherein said apparatus further comprises a mirror disposed on at least one path of the light beams divided by said beam splitter, for reflecting the received light toward the object.

7. An apparatus according to claim 3, further comprising optical path length correcting means, disposed on at least one path of the divided light beams, for defining the same optical path length for the paths of respective divided light beams.

8. An apparatus according to claim 7, wherein said optical path length correcting means comprises a transparent parallel surface plate.

9. An apparatus according to claim 3, wherein each of said plurality of light receiving means comprise stop means for blocking light from any portion of the object, other than the portion of the object to be inspected.

10. An apparatus according to claim 3, further comprising a scanning optical system for scanningly deflecting the light from said light source, and said light dividing means comprising means for receiving light deflected by said scanning optical system.

11. An apparatus according to claim 3, wherein the object is a light transmissive article, and said apparatus further comprises means for measuring the state of first and second surfaces of the light transmissive article by scanning the first surface of the article with a first light beam of the divided light beams, while scanning the second surface of the article with a second light beam of the divided light beams, wherein first light receiving means of said plurality of light receiving means comprises means for receiving light from a portion of the first surface being scanned with the first light beam, while second light receiving means of said plurality of light receiving means comprises means for receiving light from a portion of the second surface being scanned with the second light beam, said second light receiving means having an optical axis intersecting with the first light beam at a position outside an interval between the first and second surfaces.

12. An apparatus for inspecting the surface of an object, said apparatus comprising:

a light source for producing light;

a beam splitter for dividing the light from said light source into a plurality of light beams to irradiate the object along different light paths at the same time, wherein the light paths of the divided light beams have the same optical path length; and a plurality of detectors for receiving light beams from zones on the object irradiated with the divided light beams and for producing outputs on the basis of which the surface of the object can be inspected.

* * * * *

UNITED STATES PATENT AND TRADEMARK OFFICE
CERTIFICATE OF CORRECTION

PATENT NO. : 5,017,798
DATED : May 21, 1991
INVENTOR(S) : Eiichi Murakami, et al.

It is certified that error appears in the above-identified patent and that said Letters Patent is hereby corrected as shown below:

ON THE COVER PAGE

IN FOREIGN APPLICATION PRIORITY DATA

"Feb. 14, 1986 [JP] Japan ..... 61-03062" should read --Feb. 14, 1986 [JP] Japan ..... 61-30362--.

IN THE ABSTRACT

Line 2, "on" should read --an--.

COLUMN 2

Line 18, "are" should be deleted.

COLUMN 5

Line 13, "of pellicle protecting film 21b" should read --of the lower pellicle protecting film 21b--; and
Line 55, "light," should read --light--.

UNITED STATES PATENT AND TRADEMARK OFFICE
CERTIFICATE OF CORRECTION

PATENT NO. : 5,017,798

DATED : May 21, 1991

INVENTOR(S) : Eiichi Murakami, et al.

It is certified that error appears in the above-identified patent and that said Letters Patent is hereby corrected as shown below:

COLUMN 6

Line 17, "since," should read --since--.

COLUMN 7

Line 8, "FIG. 3, of" should read --FIG. 3, each of--.

COLUMN 9

Line 12, "reticle 1," should read --reticle 18,--.

COLUMN 16

Line 59, "with certain" should read --with a certain--.

Signed and Sealed this

Eighth Day of December, 1992

Attest:

DOUGLAS B. COMER

*Attesting Officer*   *Acting Commissioner of Patents and Trademarks*